United States Patent
Ito et al.

(10) Patent No.: US 9,134,010 B2
(45) Date of Patent: Sep. 15, 2015

(54) LIGHT SOURCE APPARATUS

(71) Applicant: OLYMPUS CORPORATION, Tokyo (JP)

(72) Inventors: Takeshi Ito, Hino (JP); Hiroyuki Kamee, Koganei (JP); Yoshie Aikawa, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/079,913

(22) Filed: Nov. 14, 2013

(65) Prior Publication Data

US 2014/0071691 A1  Mar. 13, 2014

Related U.S. Application Data

(63) Continuation of application No. PCT/JP2012/063526, filed on May 25, 2012.

(30) Foreign Application Priority Data

May 27, 2011 (JP) ................................. 2011-119146
May 27, 2011 (JP) ................................. 2011-119147

(51) Int. Cl.
  *F21V 7/00* (2006.01)
  *F21V 13/02* (2006.01)
  *A61B 1/06* (2006.01)
  (Continued)

(52) U.S. Cl.
  CPC ............... *F21V 13/02* (2013.01); *A61B 1/0661* (2013.01); *F21V 13/04* (2013.01); *F21V 13/10* (2013.01); *G02B 6/0008* (2013.01)

(58) Field of Classification Search
  CPC ....... A61B 1/0661; F21V 13/02; F21V 13/04; F21V 13/10; G02B 6/0008
  USPC ............ 362/551, 555, 308, 558, 560, 84, 231
  See application file for complete search history.

(56) References Cited

U.S. PATENT DOCUMENTS 7,758,224 B2 * 7/2010 Hama et al. ................... 362/555
7,980,745 B2 * 7/2011 Shanbaky ..................... 362/581
(Continued)

FOREIGN PATENT DOCUMENTS

JP  10-286234 A  10/1998
JP  10286235 A  10/1998
(Continued)

OTHER PUBLICATIONS

International Search Report dated Aug. 28, 2012 issued in PCT/JP2012/063526.
(Continued)

*Primary Examiner* — Ali Alavi
(74) *Attorney, Agent, or Firm* — Scully, Scott, Murphy & Presser, P.C.

(57) ABSTRACT

A light source apparatus includes a primary light source that emits primary light, a diffusing member that diffuses and converts the primary light into diffused light, a reflection portion that regularly reflects or diffuse-reflects and converts the diffused light into reflected light, and an emission portion that emits the reflected light to an outside. A portion of the primary light is converted in an order of the diffused light and the reflected light and emitted to the outside from the emission portion in a state of the reflected light.

35 Claims, 8 Drawing Sheets

(51) Int. Cl.
*F21V 8/00* (2006.01)
*F21V 13/04* (2006.01)
*F21V 13/10* (2006.01)

(56) References Cited

U.S. PATENT DOCUMENTS

| | | | |
|---|---|---|---|
| 8,358,067 B2 * | 1/2013 | Kamee et al. | 313/583 |
| 8,488,930 B2 * | 7/2013 | Papac et al. | 385/116 |
| 8,801,204 B2 * | 8/2014 | Kamee et al. | 362/84 |
| 2003/0201451 A1 | 10/2003 | Suehiro et al. | |
| 2009/0244922 A1 | 10/2009 | Hayakawa et al. | |
| 2009/0295266 A1 | 12/2009 | Ramer et al. | |
| 2010/0259918 A1 | 10/2010 | Rains, Jr. et al. | |
| 2012/0013811 A1 | 1/2012 | Shimizu | |
| 2012/0051693 A1 | 3/2012 | Yosida et al. | |

FOREIGN PATENT DOCUMENTS

| | | |
|---|---|---|
| JP | 11-339526 A | 12/1999 |
| JP | 2001-208904 A | 8/2001 |
| JP | 2003298117 A | 10/2003 |
| JP | 2005-108647 A | 4/2005 |
| JP | 2007-207572 A | 8/2007 |
| JP | 2011-049076 A | 3/2011 |
| JP | 201176763 A | 4/2011 |
| JP | 2011-129374 A | 6/2011 |
| JP | 2011-253015 A | 12/2011 |
| WO | WO 2006/038502 A1 | 4/2006 |

OTHER PUBLICATIONS

Japanese Office Action dated Feb. 3, 2015 received in Patent Application No. 2011-119146 together with an English language translation.

Japanese Office Action dated Mar. 3, 2015 received in Patent Application No. 2011-119147 together with an English language translation.

Japanese Office Action dated May 26, 2015 from related Japanese Patent Application No. 2011-119146, together with an English language translation.

Japanese Office Action dated May 26, 2015 from related Japanese Patent Application No. 2011-119147, together with an English language translation.

Extended Supplementary Partial European Search Report dated May 13, 2015 from related European Application No. 12 79 3721.7.

* cited by examiner

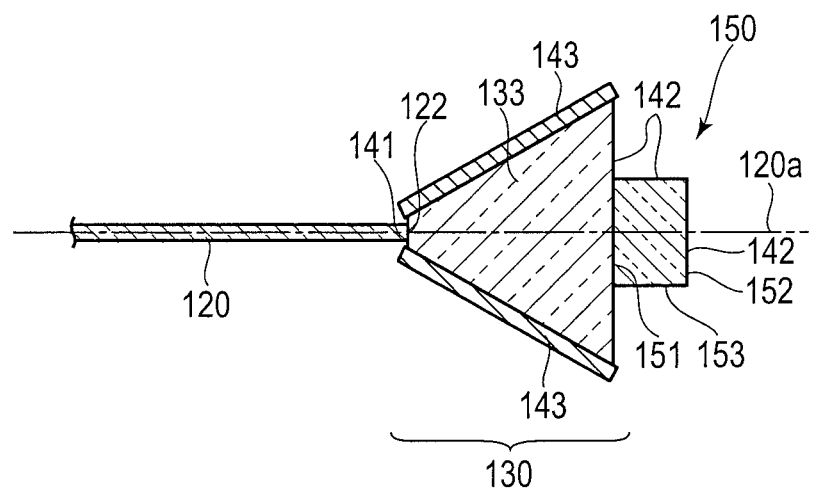
F I G. 2A
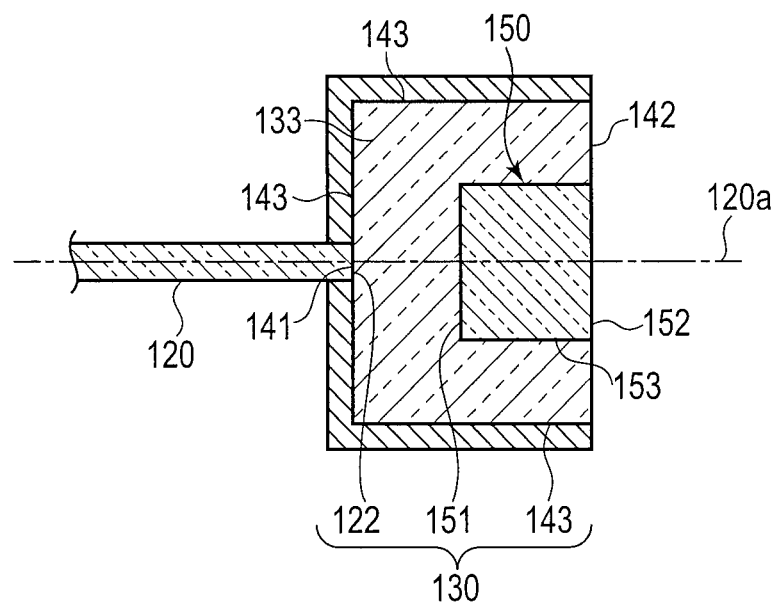
F I G. 2B

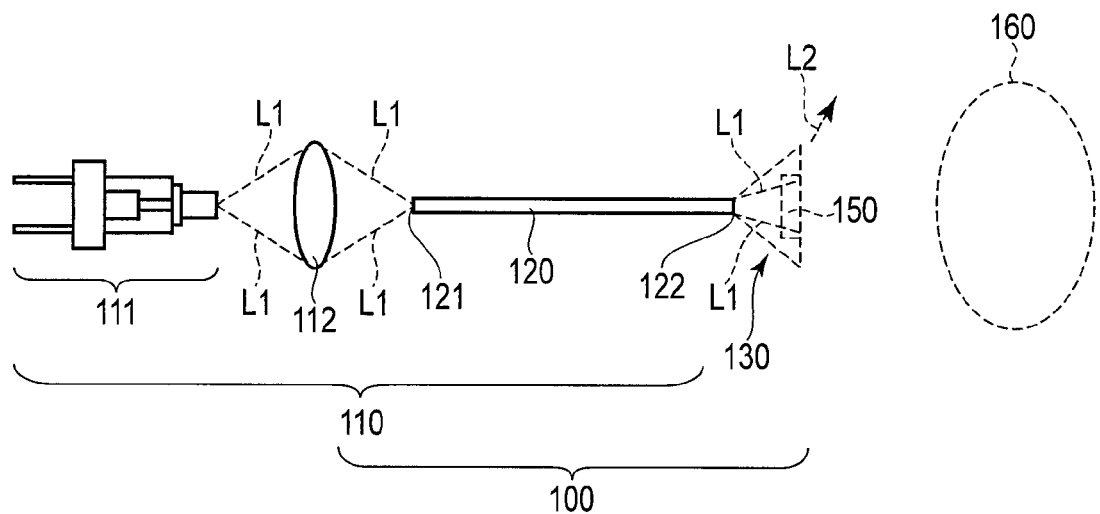
F I G. 3A
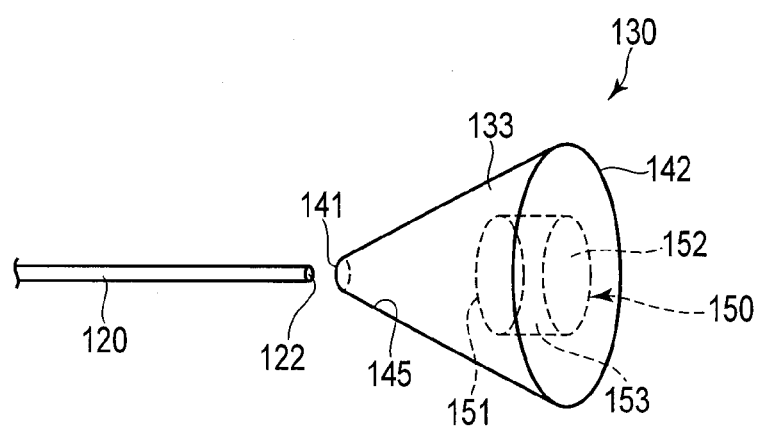
F I G. 3B

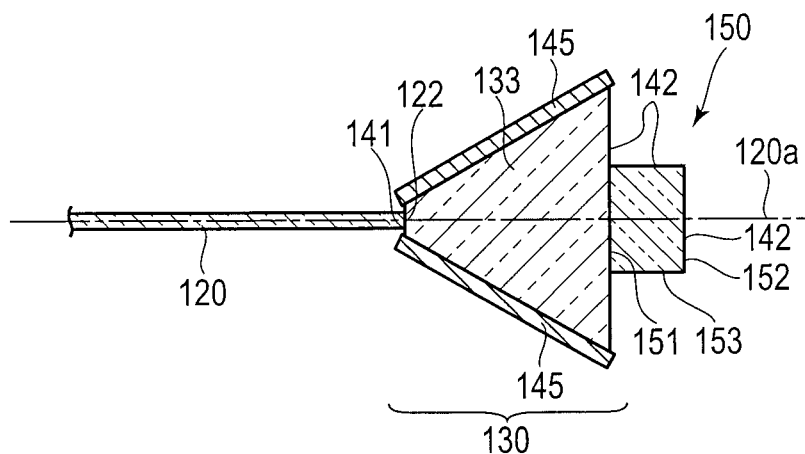
F I G. 4
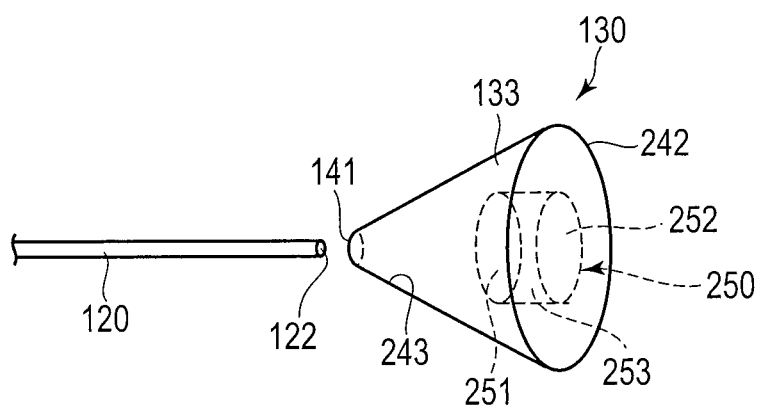
F I G. 5A

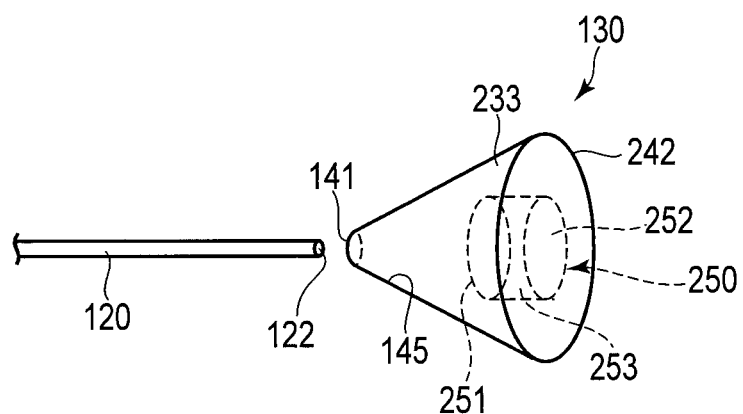
F I G. 6A
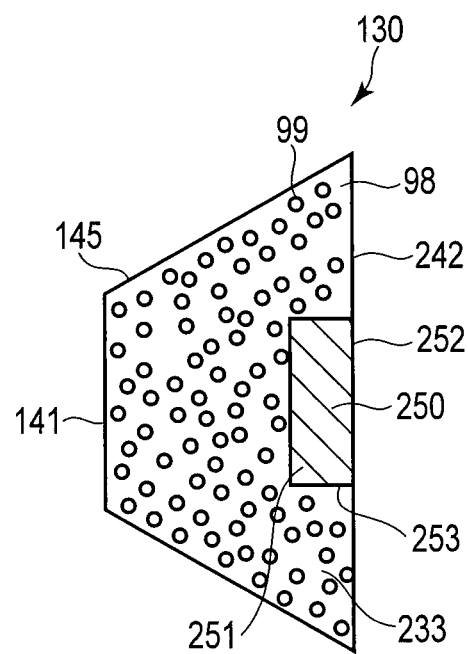
F I G. 6B

LIGHT SOURCE APPARATUS

CROSS-REFERENCE TO RELATED APPLICATIONS

This application is a Continuation Application of PCT Application No. PCT/JP2012/063526, filed May 25, 2012 and based upon and claiming the benefit of priority from prior Japanese Patent Applications No. 2011-119146, filed May 27, 2011; and No. 2011-119147, filed May 27, 2011, the entire contents of all of which are incorporated herein by reference.

BACKGROUND OF THE INVENTION

1. Field of the Invention

The present invention relates to a light source apparatus.

2. Description of the Related Art

Currently, a fiber light source combining a small solid-state light source and an optical fiber is developed. The fiber light source is used as a light source apparatus irradiating light from a tip of a thin structure.

Such a light source apparatus is disclosed by, for example, Jpn. Pat. Appln. KOKAI Publication No. 10-286234. In Jpn. Pat. Appln. KOKAI Publication No. 10-286234, an endoscope apparatus mounted with a fiber light source apparatus combining a laser light source and a diffuser is proposed.

A fiber light source apparatus 1 shown in FIG. 7 includes an He—Cd laser 20 having a trichromatic laser and an He—Ne laser 21 having a red laser. Laser light emitted from the lasers 20, 21 is guided up to a tip end portion of an endoscope 2 by a light guide 10 to irradiate an irradiation object, for example, a living organism 4 via a diffuser 11 and an illuminance distribution adjustment filter 12. In general, the light intensity of solid-state light source light including laser light as a typical example is strong on the optical axis and weak in the periphery of the optical axis. Because a solid-state light source light has coherence, a spot pattern of light called a speckle may arise on the irradiation object. These characteristics are not desirable for a light source apparatus intended for illumination. Thus, Jpn. Pat. Appln. KOKAI Publication No. 10-286234 realizes desired illumination light by laser light being diffused by the diffuser 11. That is, a light source apparatus capable of illuminating a thin lumen such as the endoscope 2 is enabled as a light source apparatus from which a desired illuminance distribution is obtained.

In the fiber light source apparatus 1 proposed in Jpn. Pat. Appln. KOKAI Publication No. 10-286234, laser light emitted from the light guide 10 irradiates the diffuser 11. The diffuser 11 has a function to diffuse and emit laser light forward. In this case, accompanying the diffusion, a portion of the laser light is also radiated backward, that is, to the side of the light guide 10. The laser light radiated backward becomes not only a loss, but also heat after being absorbed into the endoscope 2. That is, there is a possibility that the illumination light becomes darker and the temperature of the tip end portion of the fiber light source apparatus 1 rises. As a result, therefore, there is a possibility that the utilization efficiency of light is degraded near the diffuser 11.

BRIEF SUMMARY OF THE INVENTION

The present invention is made in view of such circumstances and an object thereof is to provide a light source apparatus having a diffusing function of high light utilization efficiency.

An aspect of a light source apparatus of the present invention is a light source apparatus including a primary light source that emits primary light, a diffusing member that diffuses and converts the primary light into diffused light, a reflection portion that converts the diffused light into reflected light by regular reflection or diffuse reflection, and an emission portion that emits the reflected light to an outside, wherein a portion of the primary light is converted in an order of the diffused light and the reflected light and emitted to the outside from the emission portion in a state of the reflected light.

An aspect of a light source apparatus of the present invention is a light source apparatus having a primary light source that emits primary light and a light diffusing unit that diffuses the primary light, wherein the light diffusing unit includes an incidence portion on which the primary light is incident, a diffusing member that diffuses the primary light incident from a side of the incidence portion as diffused light and emits a portion of the diffused light to the side of the incidence portion, a reflection portion that regularly reflects or diffuse-reflects the diffused light, and an emission portion that emits the diffused light to an outside, wherein the emission portion has a window portion so that the portion of the diffused light regularly reflected or diffuse-reflected by the reflection portion is emitted to the outside without reentering the diffusing member from the emission portion.

An aspect of a light source apparatus of the present invention is a light source apparatus including a primary light source that emits primary light, a first optical function member on which the primary light is incident and which turns a traveling direction of the primary light, a second optical function member that turns the traveling direction of the primary light whose traveling direction has been turned by the first optical function member, a third optical function member disposed on an optical path of the primary light showing a region between the first optical function member and the second optical function member and traveling from the first optical function member toward the second optical function member, and a window portion through which, when a portion of the primary light passes through the first optical function member, the third optical function member, and the second optical function member in this order, the portion of the primary light is emitted to an outside without reentering the first optical function member, wherein at least one of the first optical function member, the second optical function member, and the third optical function member has a diffusing function to diffuse the primary light.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is an enlarged perspective view of the light diffusing unit and the light guiding member according to a first modification of the present embodiment.

FIG. 2B is an enlarged perspective view of the light diffusing unit and the light guiding member according to a second modification of the present embodiment.

FIG. 3A is a schematic diagram of the light source apparatus according to a second embodiment of the present invention.

FIG. 3B is an enlarged perspective view of the light diffusing unit and the light guiding member.

FIG. 4 is an enlarged perspective view of the light diffusing unit and the light guiding member according to a modification of the present embodiment.

FIG. 5A is a schematic diagram of the light source apparatus according to a third embodiment of the present invention.

FIG. 6A is a schematic diagram of the light source apparatus according to a fourth embodiment of the present invention.

FIG. 6B is an enlarged perspective view of the light diffusing unit.

DETAILED DESCRIPTION OF THE INVENTION

Embodiments of the present invention will be described in detail below with reference to drawings.

First Embodiment

[Configuration]

Figure 1A:
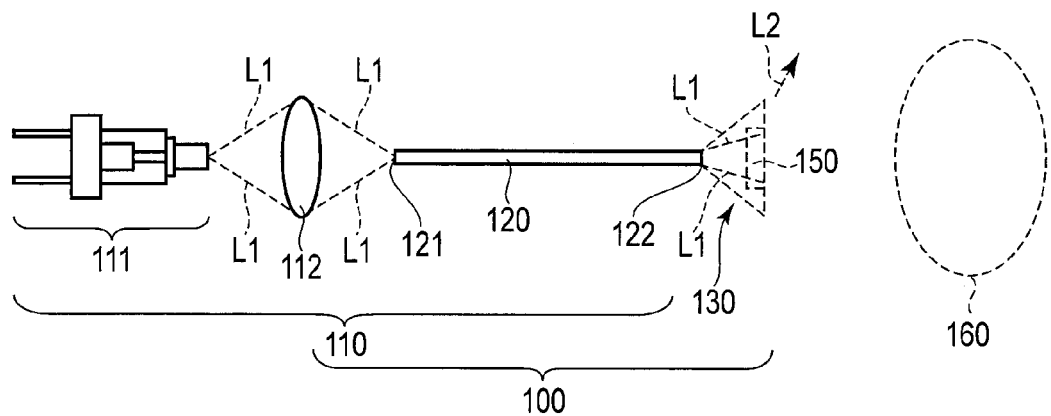
FIG. 1A is a schematic diagram of a light source apparatus according to a first embodiment of the present invention.
Figure 1B:
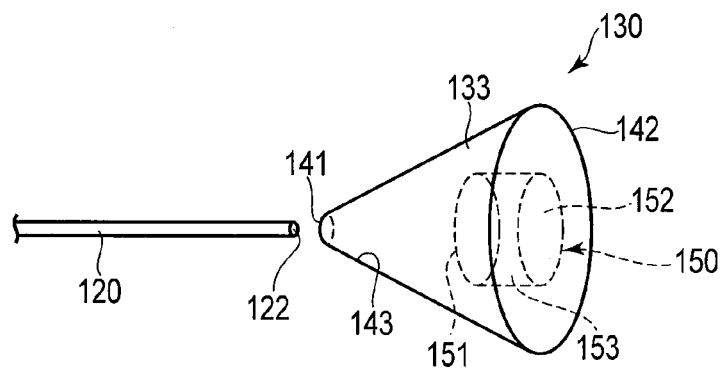
FIG. 1B is an enlarged perspective view of a light diffusing unit and a light guiding member.
Figure 1C:
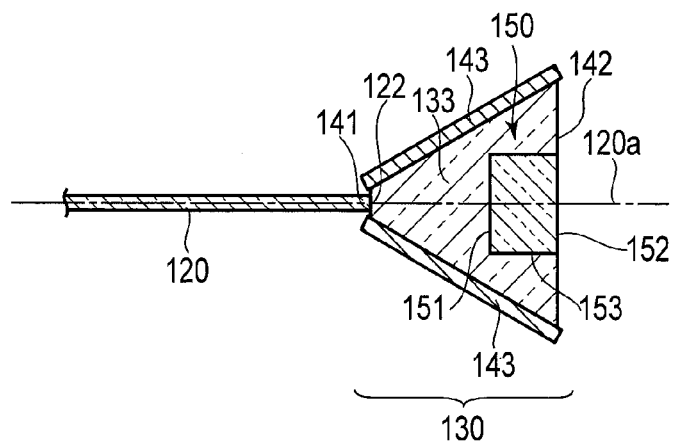
FIG. 1C is an enlarged perspective view of the light diffusing unit and the light guiding member.

The first embodiment will be described with reference to FIGS. 1A, 1B, and 1C. In FIGS. 1A and 1B, the illustration of a portion of members is omitted. In FIG. 1B, a light guiding member 120 and an incidence portion 141 of a light diffusing unit 130 are shown with a space therebetween.

[Light Source Apparatus 100]

The light source apparatus 100 mainly includes a primary light source 110 and the light diffusing unit 130. The light source apparatus 100 is configured to irradiate a diffusing member 150 disposed inside the light diffusing unit 130 with primary light L1 emitted from the primary light source 110. Next, a detailed structure of each unit will be described.

[Primary Light Source 110]

The primary light source 110 includes a semiconductor laser light source 111 that emits the primary light L1, a condenser lens 112 that condenses the primary light L1 emitted from the semiconductor laser light source 111, and the light guiding member 120 as a light guide path that guides the primary light L1 condensed by the condenser lens 112 to the diffusing member 150.

The condenser lens 112 condenses the primary light L1 on a primary light incidence end 121 of the light guiding member 120.

As the light guiding member 120, for example, a multi-mode optical fiber having a core diameter of 50 μm and a numerical aperture FNA=0.2 is used. The light guiding member 120 includes the primary light incidence end 121 on which the primary light L1 condensed by the condenser lens 112 is incident and a primary light emission end 122 from which the primary light L1 as light source light is emitted to the diffusing member 150.

[Light Diffusing Unit 130]

The light diffusing unit 130 includes the incidence portion 141 on which the primary light L1 emitted from the primary light emission end 122 is incident and an emission portion 142 having a function to emit desired illumination light to an external irradiation object 160. The light diffusing unit 130 also includes the diffusing member 150 and a light transmission member 133 and diffuses and emits the primary light L1 guided by the light guiding member 120 as a desired diffused light L2.

[Diffusing Member 150]

The diffusing member 150 has a function to convert incident light incident on the diffusing member 150 into the diffused light L2 in which the angle of divergence is broadened and coherence is lowered without changing the wavelength thereof. The diffusing member 150 has a function to diffuse the primary light L1 irradiated from the side of the incidence portion 141 as the diffused light L2 and to emit a portion of the diffused light L2 to the side of the incidence portion 141. The diffusing member 150 also has a function to allow a portion of the primary light L1 to transmit and to emit the light as a transmitted diffused light. The diffusing member 150 has, for example, a cylindrical shape. The diffusing member 150 as described above has a first region 151 facing the primary light emission end 122 of the light guiding member 120, a third region 152 opposed to the first region 151, and a second region 153 as a side face sandwiched between the first region 151 and the third region 152. The first region 151 is spaced from the primary light emission end 122. The first region 151 is disposed on a center axis 120a of the light guiding member 120. The center axis 120a passes through the primary light emission end 122 and the incidence portion 141.

[Light Transmission Member 133]

The light transmission member 133 is formed to surround the first region 151 and the second region 153 of the diffusing member 150 and is in contact with the first region 151 and the second region 153 of the diffusing member 150. The light transmission member 133 has a truncated conic shape in which the incidence portion 141 is a top surface as a first surface of the small diameter of the truncated cone, the emission portion 142 is a bottom surface as a second surface of the large diameter, and the side face is a taper face. The light transmission member 133 has the diffusing member 150 inside the light transmission member 133 such that, for example, the center of the first region 151 of the diffusing member 150 is disposed on the center axis of the truncated conic shape and the third region 152 of the diffusing member 150 is disposed in the emission portion 142. The light transmission member 133 also has a property to allow both of the primary light L1 and the diffused light L2 emitted from the diffusing member 150 to transmit. A reflection portion 143 is directly formed on the side face of the light transmission member 133, that is, an inclined plane of the truncated conic shape.

[Reflection Portion 143]

The reflection portion 143 has a function to convert incident light incident on the reflection portion 143 into reflected light by regular reflection or diffuse reflection. In the present embodiment, incident light incident on the reflection portion 143 is the diffused light L2 diffused by the diffusing member 150 and reflected light emitted from the reflection portion 143 is the diffused light L2 whose traveling direction is changed by the regular reflection or diffuse reflection. An ideal reflecting surface can realize pure regular reflection or diffuse reflection, but in most cases, regular reflection components and diffuse reflection components are mixed on an actual reflecting surface. In the present invention, various kinds of the reflection portion 143 including pure regular reflection and pure diffuse reflection can be used. The reflection portion 143 close to pure regular reflection can be realized by forming a thin film of metal or the like. Accordingly, the reflection portion 143 that can easily guide more reflected light to the side of the emission portion 142 by utilizing the side face in a taper shape is realized. The reflection portion 143 close to pure diffuse reflection can be realized by applying a powder of oxide or resin. Accordingly, the reflection portion 143 that is less likely to be affected by the shape of the reflection portion 143 is realized. Incidentally, the reflection portion 143 may have a function to convert incident light into reflected light by scattering reflection.

In the present embodiment, an example in which the reflection portion 143 close to regular reflection is realized is shown, but the function and operation are approximately the same for diffuse reflection.

The reflection portion 143 in the present invention is formed on the entire side face of the light transmission member 133. Incidentally, the reflection portion 143 may be formed only in a portion of the light transmission member 133.

[Third Region 152, Emission Portion 142]

The third region 152 of the diffusing member 150 in a cylindrical shape is smaller than the emission portion 142 in area and is arranged approximately concentrically with the emission portion 142. By arranging the diffusing member 150 as described above, the diffusing member 150 is arranged by being spaced apart from the reflection portion 143 in its entire circumference. The third region 152 forms a portion of the opening face of the emission portion 142 and is positioned in the emission portion 142. That is, the emission portion 142 includes the third region 152 and another region (hereinafter, referred to as a window portion). The third region 152 is the surface of the diffusing member 150. The diffused light L2 emitted from the third region 152 is the diffused light L2 emitted directly to the outside from the surface (third region 152) of the diffusing member 150. The window portion is a portion of the emission portion 142. The window portion is a portion facing the emission portion 142 of the light transmission member 133. The window portion is disposed so that a portion of the diffused light L2 regularly reflected or diffuse-reflected by the reflection portion 143 is emitted to the outside without reentering the diffusing member 150 from the emission portion 142. The diffused light L2 emitted from the diffusing member 150 into the light transmission member 133 is converted into reflected light by the reflection portion 143 and emitted to the outside from the window portion in a state of reflected light.

[Thickness of the Diffusing Member 150]

The thickness of the diffusing member 150 is set so that the primary light L1 is converted into the desired diffused light L2. That is, the diffused light L2 is a light obtained by diffusing the primary light L1 emitted from the semiconductor laser light source 111 at a desired angle of divergence and lowering the coherence to make a speckle or the like less likely to occur. The diffusing member 150 has a thickness capable of converting the primary light L1 into such a light.

[Light Transmission Member 133, Reflection Portion 143]

In the present embodiment, the light transmission member 133 is filled between the diffusing member 150 and the reflection portion 143 and so is formed continuously from the incidence portion 141 to the emission portion 142 all around the side of the diffusing member 150. In the present embodiment, an example in which the diffusing member 150 is surrounded by the light transmission member 133 in a region that continues from the incidence portion 141 to the emission portion 142 is shown. As the gist of the present invention, the light transmission member 133 may be disposed in at least a portion of the side face of the diffusing member 150, and a portion of the light transmission member 133 may be continuously formed from the incidence portion 141 to the emission portion 142. In other words, an effect of the present invention can be obtained if the light transmission member 133 is continuously formed from the incidence portion 141 to at least a portion of the emission portion 142.

As another expression, the reflection portion 143 is optically connected to the semiconductor laser light source 111 via the condenser lens 112, the light guiding member 120, and the light transmission member 133. The reflection portion 143 is also optically connected to the primary light emission end 122, the emission portion 142, and the diffusing member 150 via the light transmission member 133 having a function to transmit the primary light L1.

[Primary Light Emission End 122]

The primary light emission end 122 is optically connected to the incidence portion 141 so that the primary light L1 enters the incidence portion 141. More specifically, the primary light emission end 122 is connected to the neighborhood of the center of the incidence portion 141 as the small-diameter first surface of the truncated cone of the light transmission member 133.

The size of the light transmission member 133 and the size of the diffusing member 150 are set so that the relative position between the primary light emission end 122 and the diffusing member 150 allows the first region 151 of the diffusing member 150 to be irradiated with substantially all the primary light L1 emitted from the primary light emission end 122. In this case, the primary light L1 emitted from the light guiding member 120 forms a beam spot smaller than the first region 151 of the diffusing member 150 on a plane containing the first region 151 of the diffusing member 150. The beam spot is defined as a region having light stronger than $1/e^2$ with respect to the maximum intensity of the primary light L1 and e is the Napier number as the base of the natural logarithm.

[Shape and Material of Each Member]

Preferred examples of the shape and material of each member will be described.

The taper angle of the light transmission member 133 is preferably 20 degrees with respect to the center axis 120a of the light guiding member 120. The diffusing member 150 is desirably a cylindrical shape having the radius of 0.17 mm. If such a structure is adopted, the distance between the incidence portion 141 and the first region 151 of the diffusing member 150 becomes about 0.6 mm. The multi-mode optical fiber described above is used as the light guiding member 120.

The light transmission member 133 is preferably formed from a transparent material such as a transparent optical resin or general glass or quartz glass. With such materials being selected, the primary light L1 and the diffused light L2 can transmit the light transmission member 133 efficiently and the light utilization efficiency can be enhanced so that much illumination light is emitted from the emission portion 142.

To form the reflection portion 143 on the side face of the light transmission member 133, it is desirable that the upper and lower surfaces of the light transmission member 133 be first masked and a reflection material be deposited or plated. For example, a metal film that is easy to form on the side face of a light transmission member and has a high reflectance with respect to visible light is desirable as the reflection material. More desirably, for example, aluminum or silver is selected as the reflection material. However, tarnishing or discoloration occurs if a reflection material of aluminum or silver is left in the air. Thus, there is the possibility of degraded reflectance. In an extreme case, tarnishing or discoloration reaches the interface with the light transmission member 133, which may degrade the function as a reflecting surface. Thus, a protective film is desirably disposed on the top surface of the reflection material formed by deposition or plating. As the protective film, for example, $SiO_2$ or copper is desirable.

A silicon resin over which particles are dispersed in a concentration of 10 wt % and is hardened by curing is cited as an example of the diffusing member 150. Particles are, for example, alumina or silica particles and the average particle diameter of particles is 8 μm. Incidentally, the average particle diameter that is substantially equal to the wavelength of the primary light L1 to about 1000 times the wavelength can be used.

A member formed from a transparent member having a different index of refraction from that of the light transmission member 133 and provided with minute irregularities on the surface of the transparent member can be cited as an example of the diffusing member 150. Incidentally, minute irregularities that are substantially equal to the wavelength of the primary light L1 to about 1000 times the wavelength can be used.

[Operation]

The operation of the primary light L1 emitted from the semiconductor laser light source 111 will be described.

The primary light L1 emitted from the semiconductor laser light source 111 is condensed on the primary light incidence end 121 by the condenser lens 112 and enters the light guiding member 120 from the primary light incidence end 121 with high efficiency.

The primary light L1 having entered the light guiding member 120 is guided inside the light guiding member 120 and emitted from the primary light emission end 122 of the light guiding member 120 toward the light transmission member 133. At this point, the primary light L1 is emitted at an angle of divergence in accordance with the numerical aperture (NA) of the light guiding member 120 and the index of refraction of the light transmission member 133.

The primary light L1 passes through the light transmission member 133 and irradiates the first region 151 of the diffusing member 150. In this case, the first region 151 of the diffusing member 150 is formed so as to be larger than a beam spot formed by the primary light L1 on a plane containing the first region 151 of the diffusing member 150. Thus, most of the primary light L1 irradiates the diffusing member 150. As a result, there is almost no primary light L1 that is directly emitted to the outside without going through the diffusing member 150.

The primary light L1 diffuses while irradiating the diffusing member 150 and passing through the diffusing member 150 and is converted by the diffusing member 150 into the diffused light L2 having the same wavelength as the primary light L1, but having a wider angle of radiation and lower coherence. At this point, the diffused light L2 not only passes through the diffusing member 150, but also is emitted toward the incident side of the primary light L1, that is, the light transmission member 133. As a result, a portion of the diffused light L2 having passed through the diffusing member 150 is emitted to the outside from the emission portion 142 (or third region 152) in the state of the diffused light L2 to irradiate the external irradiation object 160. Another portion of the diffused light L2 is emitted from the second region 153 or the first region 151 of the diffusing member 150 so as to travel toward the light transmission member 133.

A portion of the diffused light L2 traveling toward the light transmission member 133 is reflected by the reflection portion 143 formed on the side face of the light transmission member 133 after passing through the light transmission member 133. The reflection portion 143 is a taper surface open to the emission side of illumination light, that is, the side of the irradiation object 160. Thus, the diffused light L2 reflected by the reflection portion 143 has, when compared with the original traveling direction, more components traveling toward the emission side of illumination light.

More specifically, in the diffused light L2 reflected by the reflection portion 143, a portion of the diffused light L2 travels toward the reflection portion 143 again, another portion of the diffused light L2 travels toward the diffusing member 150, and a remaining portion of the diffused light L2 is emitted to the outside from the window portion of the emission portion 142 via the light transmission member 133 in the state of reflected light to irradiate the external irradiation object 160.

In the diffused light L2 traveling to the reflection portion 143 again after being reflected once by the reflection portion 143, a portion of the diffused light L2 repeats the above process to travel to the reflection portion 143 again, another portion of the diffused light L2 travels toward the diffusing member 150, and a remaining portion of the diffused light L2 is emitted to the outside from the window portion of the emission portion 142.

Subsequently, the diffused light L2 traveling toward the reflection portion 143 or the diffusing member 150 repeats the above process.

[Operation/Effect]

Figure 7:
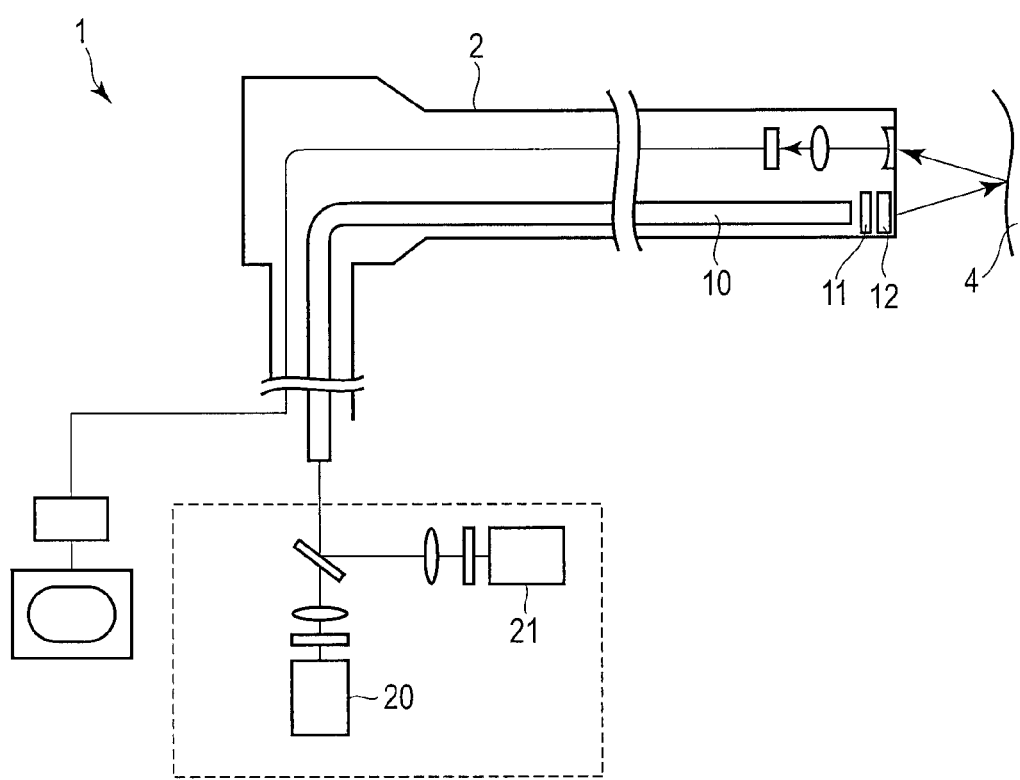
FIG. 7 is a schematic diagram of a conventional light source apparatus.

As described above, a portion of the diffused light L2 emitted from the second region 153 and the first region 151 of the diffusing member 150 is emitted to the outside from the emission portion 142 by passing through the light transmission member 133 without directly reentering the diffusing member 150. Thus, in the present embodiment, when compared with the diffuser 11 as a transmission diffusing member shown in FIG. 7, the reduced light intensity due to self-absorption of the diffusing member 150 is small. Thus, in the present embodiment, the utilization efficiency of the primary light L1 is high and the light source apparatus 100 with high fetch efficiency of the diffused light L2 can be realized. Particularly, when the degree of diffusion should be increased, the diffused light L2 is emitted at a high rate from the first region 151 where the primary light L1 is directly irradiated. A portion of the diffused light L2 emitted from the first region 151 is emitted to the light transmission member 133 disposed on the side of the primary light source 110 from the diffusing member 150. Then, a portion of the diffused light L2 travels up to the emission portion 142 via the reflection portion 143 and the light transmission member 133 and can irradiate the external irradiation object 160 in a state of high light utilization efficiency without entering the diffusing member 150 from the emission portion 142 (window portion).

In the diffused light L2 reflected by the reflection portion 143, a portion of the diffused light L2 travels toward the reflection portion 143 again and another portion of the diffused light L2 reenters the diffusing member 150. A portion of the diffused light L2 repeats the above process.

Because the reflection portion 143 and the diffusing member 150 are spaced all around the side of the diffusing member 150, the rate of the diffused light L2 emitted from the emission portion 142 without reentering the diffusing member 150 is increased and the light utilization efficiency is further enhanced.

Because the light transmission member 133 is made of glass or resin having high transmittance with respect to the primary light L1 and the diffused light L2, the loss of the primary light L1 and the diffused light L2 caused by the light transmission 133 is small and the light utilization efficiency is further enhanced.

The light transmission member 133 has a truncate conic shape from the incidence portion 141 to the emission portion 142. Thus, each time the diffused light L2 is reflected by the reflection portion 143 formed all around the side face, the emission direction is directed toward the emission portion 142 and the light utilization efficiency is further enhanced.

The diffusing member 150 has a cylindrical shape and the first region 151 is larger than a beam spot of the primary light L1. Thus, the primary light L1 irradiates the diffusing member 150 and is efficiently converted into the diffused light L2 by the diffusing member 150 and the light utilization efficiency is further enhanced.

The reflection portion 143 is formed all around side face of the light transmission member 133. Thus, the diffused light L2 can be prevented from being emitted to the outside from a portion other than the emission portion 142 and being absorbed by other members so that the diffused light L2 can efficiently be emitted from the emission portion 142.

A metal having a high reflectance with respect to the visible light is used for the reflection portion 143. Thus, the absorption during reflection by the reflection portion 143 is small, resulting in a small light loss and high utilization efficiency.

The reflection portion 143 is directly formed on the side face of the light transmission member 133. Thus, the diffused light L2 is not leaked to the outside of the light transmission member 133 and is not affected during reflection by a structure outside the reflection film. As a result, when compared with a configuration in which the reflection portion 143 and the light transmission member 133 are produced separately and the reflection portion 143 is bonded to the light transmission member 133, the diffused light L2 can be reflected by the reflection portion 143 with high efficiency without passing through an adhesive or the like in the present embodiment, resulting in a small light loss and high utilization efficiency.

In the present embodiment, the light transmission member 133 and the diffusing member 150 are in contact in two regions of the first region 151 and the second region 153. Thus, the diffusing member 150 can be prevented from dropping from the light transmission member 133 so that a light source apparatus 100 with high reliability can be provided.

By adopting the above configuration, the light source apparatus 100 having high utilization efficiency of the primary light L1 and high fetch efficiency of the diffused light L2 can be provided.

Also, by adopting the above configuration, a light diffusing unit with high light utilization efficiency that broadens the angle of radiation so that laser light has an illuminance distribution appropriate for illumination light and realizes the diffused light L2 that is less likely to cause a speckle by lowering coherence. Accordingly, when compared with a case of the light intensity of the primary light L1 emitted from the primary light source 110, the light source apparatus 100 that is brighter and generates less heat at the tip end portion can be realized.

In the present invention, an example of combining the semiconductor laser light source 111, the condenser lens 112, and the light guiding member 120 as a light guide path is shown as the primary light source 110, but the present invention is not limited to such an example. The primary light source 110 can be replaced by a solid-state light source such as a light-emitting diode and super luminescent diode (SLD), a solid state laser, a gas laser or the like. The light guiding member 120 can be replaced by a bundle fiber in which a plurality of optical fibers is bundled or a general film or slab waveguide in which a light guide path is formed by providing a distribution of the index of refraction on a resin substrate or semiconductor substrate. Further, the incidence end of the light guide path can be directly joined to the light-emitting surface of the semiconductor laser light source 111, a light-emitting diode, SLD or the like without using the condenser lens 112. In addition, these can appropriately be combined.

First Modification of the First Embodiment

In the present modification, as shown in FIG. 2A, a diffusing member 150 is disposed in contact with the surface on the side of an emission portion 142 of a light transmission member 133 in a truncated conic shape. In this case, the emission portion 142 represents the bottom face of the light transmission member 133 where a first region 151 of the diffusing member 150 is not in contact and all outer surfaces of the diffusing member 150 excluding the first region 151. The diffused light L2 is emitted to the outside from all curved faces formed from the bottom face and outer surfaces. The first region 151 is in contact with the light transmission member 133 and a second region 153 and a third region 152 are positioned on the emission portion 142. Thus, the emission portion 142 includes the second region 153, the third region 152, and a window portion.

By adopting such a structure, the shape of the light transmission member is made simpler, which makes it easier to produce the light transmission member.

In the modification of the present embodiment, a structure in which the light transmission member 133 and the diffusing member 150 are in contact only in the first region 151 is adopted and therefore, a light source apparatus 100 that can easily be produced can be provided.

Second Modification of the First Embodiment

In the above embodiment, the entire light transmission member 133 has a truncated conic shape and the reflection portion 143 is disposed on the side face of the truncated cone, which is a taper surface, but the present embodiment is not limited to such an example.

In the present modification, as shown in FIG. 2B, for example, a light transmission member 133 may have a cylindrical shape. In this case, a reflection portion 143 is desirably disposed not only on the side face of the light transmission member 133, but also in a region of the bottom face of the cylinder excluding an incidence portion 141 on which primary light guided by a light guiding member 120 is incident.

Second Embodiment

[Configuration]

Figure 3C:
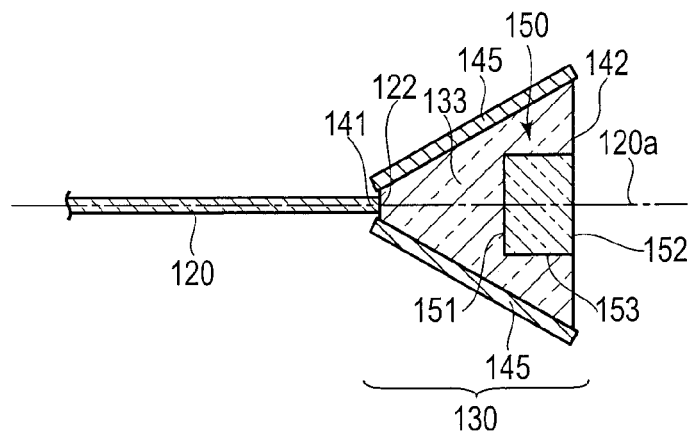
FIG. 3C is an enlarged perspective view of the light diffusing unit and the light guiding member.

The second embodiment will be described with reference to FIGS. 3A, 3B, 3C, 3D, and 3E. In FIGS. 3A and 3B, the illustration of a portion of members is omitted. In FIG. 3B, a light guiding member 120 and an incidence portion 141 of a light diffusing unit 130 are shown with a space therebetween.

[Light Source Apparatus 100, Primary Light Source 110]

A Light source apparatus 100 and a primary light source 110 are configured in the same manner as in the first embodiment.

[Light Diffusing Unit 130]

The light diffusing unit 130 includes the incidence portion 141 on which primary light L1 emitted from a primary light emission end 122 is incident and an emission portion 142 having a function to emit desired illumination light to an external irradiation object 160. The light diffusing unit 130 also includes a reflection diffusing member 150 as a first optical function member and a light transmission member 133 as a third optical function member and diffuses and emits the primary light L1 guided by the light guiding member 120 as desired diffused light L2. A second optical function member will be described later.

[Diffusing Member 150]

The diffusing member 150 has a function to convert incident light incident on the diffusing member 150 into the diffused light L2 in which the angle of divergence is broadened and coherence is lowered without changing the wavelength thereof. The diffusing member 150 has a function to diffuse the primary light L1 irradiated from the side of the incidence portion 141 as the diffused light L2 and to emit a portion of the diffused light L2 to the side of the incidence portion 141. The diffusing member 150 has, for example, a cylindrical shape. The diffusing member 150 as described above has a first region 151 facing the primary light emission end 122 of the light guiding member 120, a third region 152 opposed to the first region 151, and a second region 153 as a side face sandwiched between the first region 151 and the third region 152. The first region 151 is spaced apart from the primary light emission end 122. The first region 151 is disposed on a center axis 120a of the light guiding member 120. The center axis 120a passes through the primary light emission end 122 and the incidence portion 141.

[Light Transmission Member 133]

The light transmission member 133 is formed to surround the first region 151 and the second region 153 of the diffusing member 150 and is in contact with the first region 151 and the second region 153 of the diffusing member 150. The light transmission member 133 is a three-dimensional object in a truncated conic shape in which the incidence portion 141 is a top surface as a first surface of the small diameter of the truncated cone, the emission portion 142 is a bottom surface as a second surface of the large diameter, and the side face is a taper face. The light transmission member 133 has the diffusing member 150 inside the light transmission member 133 such that, for example, the center of the first region 151 of the diffusing member 150 is disposed on the center axis of the truncated conic shape and the third region 152 of the diffusing member 150 is disposed in the emission portion 142. The light transmission member 133 is disposed in at least a portion of the space inside the three-dimensional object. The light transmission member 133 also has a property to allow both of the primary light L1 and the diffused light L2 emitted from the diffusing member 150 to transmit. A regular reflection portion 145 as the second optical function member is directly formed on the side face of the light transmission member 133, that is, an inclined plane of the truncated conic shape. The regular reflection portion 145 only needs to be disposed in at least a portion of the side face of the three-dimensional object.

[Regular Reflection Portion 145]

The regular reflection portion 145 has a function to regularly reflect and convert incident light incident on the regular reflection portion 145 into reflected light. In the present embodiment, incident light incident on the regular reflection portion 145 is the diffused light L2 whose traveling direction is turned by being diffused by the diffusing member 150. Also, reflected light emitted from the regular reflection portion 145 is the diffused light L2 whose traveling direction is turned by being regularly reflected by the regular reflection portion 145. In the regular reflection portion 145 and the diffusing member 150, an ideal reflecting surface can realize pure regular reflection or diffuse reflection, but in most cases, regular reflection components and diffuse reflection components are mixed on an actual reflecting surface. In the present invention, the diffusing member 150 means a member having a reflection function in which the diffuse reflection is mainly dominant, including pure regular reflection. In addition, the regular reflection portion 145 means a member having a reflection function in which the regular reflection is mainly dominant, including pure regular reflection. The regular reflection portion 145 close to pure regular reflection can be realized by forming a thin film of metal or the like. Accordingly, the regular reflection portion 145 that can easily guide more reflected light to the side of the emission portion 142 by utilizing the side face in a taper shape is realized. The regular reflection portion 145 close to pure diffuse reflection can be realized by applying a powder of oxide or resin. Accordingly, the regular reflection portion 145 that is less likely to be affected by the shape of the regular reflection portion 145 is realized.

The regular reflection portion 145 in the present invention is formed on the entire side face of the light transmission member 133. Incidentally, the regular reflection portion 145 may be formed only in a portion of the taper surface of the light transmission member 133.

[Third Region 152, Emission Portion 142]

The third region 152 of the diffusing member 150 in a cylindrical shape is smaller than the emission portion 142 in area and is arranged approximately concentrically with the emission portion 142. By arranging the diffusing member 150 as described above, the diffusing member 150 is arranged by being spaced apart from the regular reflection portion 145 in its entire circumference. The third region 152 forms a portion of the opening face of the emission portion 142. That is, the emission portion 142 includes the third region 152 and another region (hereinafter, referred to as a window portion). The third region 152 is the surface of the diffusing member 150. In the present embodiment, the diffusing member 150 does not allow the primary light L1 to transmit and the primary light L1 emitted from the diffusing member 150 is totally diffuse-reflected toward the light transmission member 133. The window portion is a portion facing the emission portion 142 of the light transmission member 133. The window portion is a portion of the emission portion 142. The window portion is disposed so that when a portion of the primary light L1 passes through the first optical function member (diffusing member 150), the third optical function member (light transmission member 133), and the second optical function member (regular reflection portion 145) in this order, a portion of the diffused light L2 regularly reflected by the regular reflection portion 145 is emitted to the outside without reentering the diffusing member 150. The diffused light L2 emitted from the diffusing member 150 into the light transmission member 133 is converted into reflected light by the regular reflection portion 145 and emitted to the outside from the window portion in a state of reflected light.

[Light Transmission Member 133, Regular Reflection Portion 145]

In the present embodiment, the light transmission member 133 is filled between the diffusing member 150 and the regular reflection portion 145 and so is formed continuously from the incidence portion 141 to the emission portion 142 all around the side of the diffusing member 150. In the present embodiment, an example in which the diffusing member 150 is surrounded by the light transmission member 133 in a region that continues from the incidence portion 141 to the emission portion 142 is shown. As the gist of the present invention, the light transmission member 133 may be disposed in at least a portion of the side face of the diffusing member 150, and a portion of the light transmission member 133 may be continuously formed from the incidence portion 141 to the emission portion 142. In other words, an effect of the present invention can be obtained if the light transmission member 133 is continuously formed from the incidence portion 141 to at least a portion of the emission portion 142.

As another expression, the regular reflection portion 145 is optically connected to a semiconductor laser light source 111 via the condenser lens 112, the light guiding member 120, and the light transmission member 133. The regular reflection portion 145 is also connected to the primary light emission end 122, the emission portion 142, and the diffusing member 150 via the light transmission member 133 having a function to transmit the primary light L1.

[Primary Light Emission End 122]

The primary light emission end 122 is configured in the same manner as in the first embodiment.

[Shape and Material of Each Member]

Preferred examples of the shape and material of each member will be described.

The content described in [Shape and material of each member] in the first embodiment can be applied to the taper angle of the light transmission member 133, the shape of the diffusing member 150, and the materials of the light guiding member 120 and the light transmission member 133 in the present embodiment.

Also, the formation method of the reflection portion 143 described in [Shape and material of each member] in the first embodiment can be applied to the formation method of the regular reflection portion 145 to the side face of the light transmission member 133.

Figure 3D:
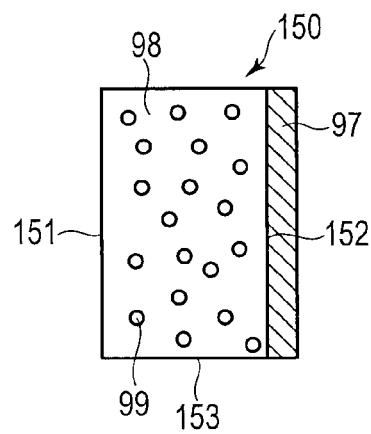
FIG. 3D is an enlarged perspective view of a diffusing member.

As shown in FIG. 3D, the diffusing member 150 is formed from, for example, a light transmission member 98 having translucency with respect to primary light and diffusion particles 99 disposed in a dispersed state inside the light transmission member 98. The above diffusing member 150 is mounted on a reflecting surface 97. The light transmission member 98 is, for example, a silicon resin that allows light to transmit. The diffusion particles 99 are, for example, alumina or silica and cause diffuse reflection of the primary light L1. The average particle diameter the diffusion particles 99 is, for example, 8 μm. Incidentally, the average particle diameter that is substantially equal to the wavelength of the primary light L1 to about 1000 times the wavelength can be used. In this case, the light transmission member 98 is exposed in the first region 151 and the second region 153 and the third region 152 is in contact with the reflecting surface 97.

Figure 3E:
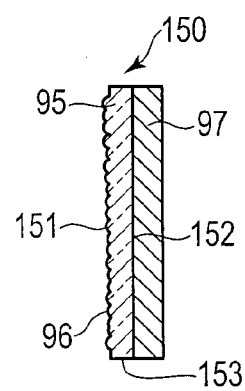
FIG. 3E is a modification of the diffusing member and an enlarged perspective view of the diffusing member.

In the diffusing member 150, as shown in FIG. 3E, a translucent member 95 having a different index of refraction from that of the light transmission member 133 may be disposed on the reflecting surface 97. The translucent member 95 has minute irregularities 96 disposed on the surface of the translucent member 95. The minute irregularities 96 that are substantially equal to the wavelength of the primary light L1 to about 1000 times the wavelength can be used.

[Operation]

The operation of the primary light L1 emitted from the semiconductor laser light source 111 will be described.

The primary light L1 emitted from the semiconductor laser light source 111 is condensed on a primary light incidence end 121 by a condenser lens 112 and enters the light guiding member 120 from the primary light incidence end 121 with high efficiency.

The primary light L1 having entered the light guiding member 120 is guided inside the light guiding member 120 and emitted from the primary light emission end 122 toward the light transmission member 133. At this point, the primary light L1 is emitted at an angle of divergence in accordance with the numerical aperture (NA) of the light guiding member 120 and the index of refraction of the light transmission member 133.

The primary light L1 passes through the light transmission member 133 and irradiates the first region 151 of the diffusing member 150. In this case, the first region 151 of the diffusing member 150 is formed so as to be larger than a beam spot formed by the primary light L1 on a plane containing the first region 151 of the diffusing member 150. Thus, most of the primary light L1 irradiates the diffusing member 150. As a result, there is almost no primary light L1 that is directly emitted to the outside without going through the diffusing member 150.

The primary light L1 diffuses while irradiating the diffusing member 150 and traveling through the diffusing member 150 and is converted by the diffusing member 150 into the diffused light L2 having the same wavelength as the primary light L1, but having a wider angle of radiation and lower coherence. At this point, the diffused light L2 is reflected by the reflecting surface 97 and emitted toward the incident side of the primary light L1, that is, the light transmission member 133. As a result, a portion of the diffused light L2 is emitted from the second region 153 or the first region 151 of the diffusing member 150 so as to travel toward the light transmission member 133.

A portion of the diffused light L2 traveling toward the light transmission member 133 is reflected by the regular reflection portion 145 as the second optical function member formed on the side face of the light transmission member 133 after passing through the light transmission member 133. The regular reflection portion 145 is a taper surface open to the emission side of illumination light, that is, the side of the irradiation object 160. Thus, the diffused light L2 reflected by the regular reflection portion 145 has, when compared with the original traveling direction, more components traveling toward the emission side of illumination light.

More specifically, in the diffused light L2 reflected by the regular reflection portion 145, a portion of the diffused light L2 travels toward the regular reflection portion 145 again, another portion of the diffused light L2 travels toward the diffusing member 150, and a remaining portion of the diffused light L2 is emitted from the window portion of the emission portion 142 via the light transmission member 133 in the state of reflected light to irradiate the external irradiation object 160.

In the diffused light L2 traveling to the regular reflection portion 145 again after being reflected once by the regular reflection portion 145, a portion of the diffused light L2 repeats the above process to travel to the regular reflection portion 145 again, another portion of the diffused light L2 travels toward the diffusing member 150, and a remaining portion of the diffused light L2 is emitted to the outside from the window portion of the emission portion 142.

Subsequently, the diffused light L2 traveling toward the regular reflection portion 145 or the diffusing member 150 repeats the above process.

To sum up, the primary light L1 is caused to turn its traveling direction and diffuse and is also converted into the primary light L2, by the diffusing member 150 as the first optical function member. The primary light L2 travels through the light transmission member 133 as the third optical function member disposed between the first optical function member (diffusing member 150) and the second optical function member (regular reflection portion 145). The light transmission member 133 indicates a region between the first optical function member (diffusing member 150) and the second optical function member (regular reflection portion 145) and is disposed on an optical path of the primary light L1 traveling from the first optical function member (diffusing member 150) toward the second optical function member (regular reflection portion 145). A portion of the primary light L1 irradiates the second optical function member (regular reflection portion 145). The primary light L1 having irradiated the second optical function member (regular reflection portion 145) is caused to turn its traveling direction by the second optical function member (regular reflection portion 145). The primary light L1 caused to turn its traveling direction by the second optical function member (regular reflection portion 145) travels through the third optical function member (light transmission member 133) again and a portion of the primary light L1 is emitted to the outside from the window portion.

[Operation/Effect]

As described above, a portion of the diffused light L2 emitted from the first region 151 of the diffusing member 150 is emitted to the outside from the emission portion 142 by passing through the light transmission member 133 without directly reentering the diffusing member 150. Thus, in the present embodiment, when compared with the diffuser 11 as a transmission diffusing member shown in FIG. 7, the reduced light intensity due to self-absorption of the diffusing member 150 is small. Thus, in the present embodiment, the utilization efficiency of the primary light L1 is high and the light source apparatus 100 with high fetch efficiency of the diffused light L2 can be realized. Particularly when degree of diffusion should be increased, the diffused light L2 is emitted at a high rate from the first region 151 where the primary light L1 is directly irradiated. A portion of the diffused light L2 emitted from the first region 151 is emitted to the light transmission member 133 disposed on the side of the primary light source 110 from the diffusing member 150. Then, a portion of the diffused light L2 travels up to the emission portion 142 via the regular reflection portion 145 and the light transmission member 133 without entering the diffusing member 150 and can irradiate the external irradiation object 160 in a state of high light utilization efficiency.

Because the regular reflection portion 145 and the diffusing member 150 are spaced all around the side of the diffusing member 150, the rate of the diffused light L2 emitted from the emission portion 142 without reentering the diffusing member 150 is increased and the light utilization efficiency is further enhanced.

Because the light transmission member 133 is made of glass or resin having high transmittance with respect to the primary light L1 and the diffused light L2, the loss of the primary light L1 and the diffused light L2 caused by the light transmission 133 is small and the light utilization efficiency is further enhanced.

The light transmission member 133 has a truncated conic shape from the incidence portion 141 to the emission portion 142. Thus, each time the diffused light L2 is reflected by the regular reflection portion 145 formed all around the side face, the emission direction is directed toward the emission portion 142 and the light utilization efficiency is further enhanced.

The diffusing member 150 has a cylindrical shape and the first region 151 is larger than a beam spot of the primary light L1. Thus, the primary light L1 efficiently irradiates the diffusing member 150 and is converted into the diffused light L2 by the diffusing member 150 and the light utilization efficiency is further enhanced.

The regular reflection portion 145 is formed on the entire side face of the light transmission member 133. Thus, the diffused light L2 can be prevented from being emitted to the outside from a portion other than the emission portion 142 and being absorbed by other members so that the diffused light L2 can efficiently be emitted from the emission portion 142.

A metal having a high reflectance with respect to the visible light is used for the regular reflection portion 145. Thus, the absorption during reflection by the regular reflection portion 145 is small, resulting in a small light loss and high utilization efficiency.

The regular reflection portion 145 is directly formed on the side face of the light transmission member 133. Thus, the diffused light L2 is not leaked to the outside of the light transmission member 133 and is not affected during reflection by a structure outside the reflection film. As a result, when compared with a configuration in which the regular reflection portion 145 and the light transmission member 133 are produced separately and the regular reflection portion 145 is bonded to the light transmission member 133, the diffused light L2 can be reflected by the regular reflection portion 145 with high efficiency without passing through an adhesive or the like in the present embodiment, resulting in a small light loss and high utilization efficiency.

In the present embodiment, the light transmission member 133 and the diffusing member 150 are in contact in two regions of the first region 151 and the second region 153. Thus, the diffusing member 150 can be prevented from dropping from the light transmission member 133 so that a light source apparatus 100 with high reliability can be provided.

Also in the present embodiment, the diffusing member 150 is disposed on the reflecting surface 97 and the diffusion particles 99 are dispersed inside the light transmission member 98 and therefore, the primary light L1 irradiating the diffusing member 150 is not reflected before being diffused and the primary light L1 is not emitted to the outside before being diffused. Therefore, problems caused by direction emission of the primary light L1 to the outside are less likely to occur and an occurrence of speckle in the irradiation surface can be inhibited.

By adopting the above configuration, the light source apparatus 100 having a high utilization efficiency of the primary light L1 and a high fetch efficiency of the diffused light L2 can be provided.

Also, by adopting the above configuration, a light diffusing unit with high light utilization efficiency that broadens the angle of radiation so that laser light has an illuminance distribution appropriate for illumination light and realizes the diffused light L2 that is less likely to cause a speckle by lowered coherence. Accordingly, when compared with a case of the light intensity of the primary light L1 emitted from the primary light source 110, the light source apparatus 100 that is brighter and generates less heat at the tip portion can be realized.

In the present embodiment, as shown in FIG. 3D, an example configured so that the primary light L1 is not emitted to the outside without going through the light transmission member 133 by the reflecting surface 97 being disposed is shown, but the present embodiment is not limited to such an example. For example, the diffusing member 150 may be configured not to have the reflecting surface 97 so that a portion of the primary light L1 is emitted directly toward the irradiation object 160 and another portion of the primary light L1 is emitted toward the light transmission member 133. This makes the configuration of the diffusing member 150 simpler.

First Modification of the Second Embodiment

In the present modification, as shown in FIG. 4, a diffusing member 150 is disposed in contact with the surface on the side of an emission portion 142 of a light transmission member 133 in a truncated conic shape. In this case, the emission portion 142 represents the bottom face of the light transmission member 133 where a first region 151 of the diffusing member 150 is not in contact and all outer surfaces of the diffusing member 150 excluding the first region 151. The diffused light L2 is emitted to the outside from all curved faces formed from the bottom face and outer surfaces. The first region 151 is in contact with the light transmission member 133 and a second region 153 and a third region 152 are positioned on the emission portion 142. Thus, the emission portion 142 is formed from the second region 153, the third region 152, and a window portion.

By adopting such a structure, the shape of the light transmission member is made simpler, which makes it easier to produce the light transmission member.

In the modification of the present embodiment, a structure in which the light transmission member 133 and the diffusing member 150 are in contact only in the first region 151 is adopted and therefore, the light source apparatus 100 that can easily be produced can be provided.

Third Embodiment

[Configuration]

FIG. 5A shows a light diffusing unit 130 according to the third embodiment.

In the second embodiment, the first optical function member directly irradiated by the primary light L1 is the reflection diffusing member 150, the second optical function member is the regular reflection portion 145 formed on the taper surface of the light transmission member 133, and the third optical function member is the light transmission member 133 disposed between the diffusing member 150 and the regular reflection portion 145.

In the present embodiment, however, the first optical function member is a regular reflection portion 250 and the second optical function member is a reflection diffusing member 243 and these points are different from the second embodiment.

The regular reflection portion 250 in the present embodiment is formed by a top surface of a base material being coated with a reflecting surface made of metal. The regular reflection portion 250 is formed by, for example, an aluminum film as a reflection film being formed on a top surface of a glass substrate in a cylindrical shape. Instead of the aluminum film, silver or other metal films may be used.

That is, when, following the second embodiment, a first region 251, a second region 253, and a third region 252 are formed on each surface of a glass plate in a cylindrical shape of the regular reflection portion 250, an aluminum film as a reflection film is formed on the third region 252 and a glass surface is exposed in the first region 251 and the second region 253. The index of refraction of the glass may be the same as or different from that of a light transmission member 133. If the indexes of refraction are mutually different, not only the third region 252, but also the first region 251 reflects primary light L1. The primary light L1, reflected light, and diffused light L2 are refracted in the interface between the glass substrate and the light transmission member 133 and thus, optical paths are complexly tangled and it becomes easier to reduce speckles and the like.

Figure 5B:
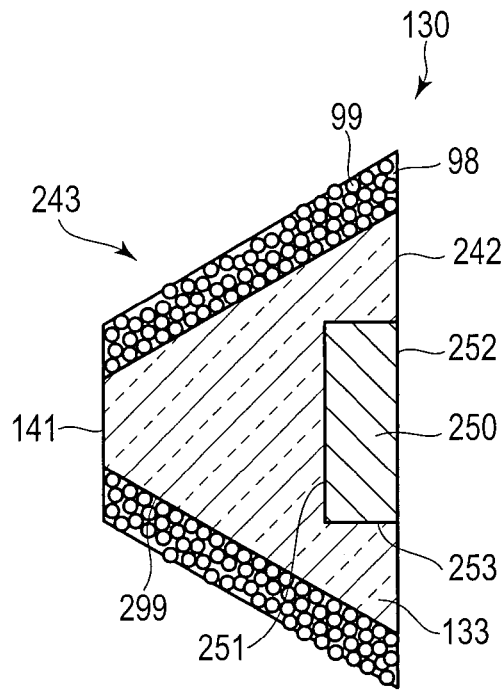
FIG. 5B is an enlarged perspective view of the light diffusing unit.
Figure 5C:
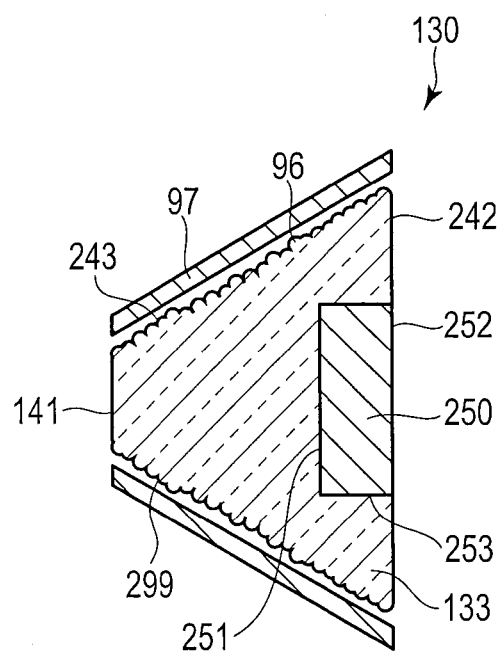
FIG. 5C is a modification of the light diffusing unit and a sectional view of the light diffusing unit.

As shown in FIG. 5B, the diffusing member 243 is formed on a taper surface 299 of the light transmission member 133. The diffusing member 243 is optically connected to at least a portion of the taper surface 299 of the light transmission member 133. The diffusing member 243 functions as a diffusing surface formed by diffusion particles 99 of silica, alumina and the like being mixed with a light transmission member 98. The diffusing member 243 is applied onto the taper surface 299 of the light transmission member 133 two-dimensionally. The diffusing member 243 may be applied to at least a portion of the taper surface 299. Because the diffusion particles 99 of silica, alumina and the like efficiently cause diffuse reflection of irradiated light, light is diffused and reflected satisfactorily even if no reflection film or the like is disposed on the taper surface 299. In one of a case when optical translucency of the diffusion particles 99 is high, a case when the thickness of the diffusion particles 99 is thin, and a case when the concentration of the diffusion particles 99 for the light transmission member 98 is low, a reflecting surface (not shown) may be disposed on the outer side of the diffusing member 243. Accordingly, the reflectance of the diffusing member 243 is improved and the optical loss caused by leakage of the primary light L1 to the outside can be reduced.

With the above configuration, the diffusing member 243 is formed on the taper surface 299 of the light transmission member 133 relatively easily.

As shown in FIG. 5G, the diffusing member 243 may also function as minute irregularities 96 formed by the surface of the light transmission member 133 being made coarse and further formed like ground glass. In this case, the diffusing member 243 has a reflecting surface 97 that reflects the primary light L1 on the surface where the minute irregularities 96 of the light transmission member 133 are formed. With the reflecting surface 97 disposed on the outer side of the diffusing member 243, the reflectance of the diffusing member 243 is improved and the optical loss caused by leakage of the primary light L1 to the outside can be reduced.

A holding member (not shown) holding the light transmission member 133 may have the above diffusing member 243 on a surface opposed to the taper surface 299.

[Operation]

The operation of the primary light L1 emitted from a semiconductor laser light source 111 will be described.

The primary light L1 emitted from the semiconductor laser light source 111 is emitted into the light transmission member 133 by an operation similar to that in the first embodiment.

The primary light L1 passes through the light transmission member 133 and irradiates the third region 252 via the first region 251 of the regular reflection portion 250. In this case, the third region 252 is formed so as to be larger than a beam spot formed by the primary light L1 on a plane containing the third region 252. Thus, most of the primary light L1 irradiates the third region 252 of the regular reflection portion 250 as a reflecting surface. As a result, there is almost no primary light L1 that is directly emitted to the outside without going through the regular reflection portion 250.

The primary light L1 is reflected by the regular reflection portion 250 and emitted toward the incident side of the primary light L1, that is, the light transmission member 133.

A portion of the reflected light emitted toward the light transmission member 133 is diffuse-reflected by the diffusing member 243 formed on the side face of the light transmission member 133 after passing through the light transmission member 133. The diffusing member 243 is a taper surface open to the emission side of illumination light, that is, the side of an irradiation object 160. Thus, the diffused light L2 diffuse-reflected by the diffusing member 243 has, when compared with the original traveling direction, more components traveling toward the emission side of illumination light.

To sum up, the primary light L1 is caused to turn the traveling direction by the regular reflection portion 250 as the first optical function member. The primary light L1 travels through the light transmission member 133 as the third optical function member arranged between the first optical function member (regular reflection portion 250) and the second optical function member (diffusing member 243). A portion of the primary light L1 irradiates the second optical function member (diffusing member 243). The primary light L1 having irradiated the second optical function member (diffusing member 243) is caused to turn its traveling direction and diffuse and is also converted into the diffused light L2, by the second optical function member (diffusing member 243). The diffused light L2 travels through the third optical function member (light transmission member 133) again and a portion of the diffused light L2 is emitted to the outside from the window portion.

[Operation]

By adopting the above configuration, the primary light L1 is efficiently reflected by the regular reflection portion 250 and passes through the light transmission member 133 to widely irradiate the diffusing member 243 formed on the taper surface 299. The primary light L1 widely irradiating the diffusing member 243 is reflected and diffused by the diffusing member 243 as a wide region and emitted to the outside from the window portion of an emission portion 242 as the diffused light L2.

[Effect]

By the configuration of the present embodiment, when compared with the second embodiment, the area of a region of reflection and diffusion can be increased. In general, when compared with the regular reflection, the diffuse reflection absorbs light and the absorbed light is converted into heat. By increasing the area of a region of diffuse reflection like in the present embodiment, local heating can be reduced. The diffusing member 243 is close to a holding member (not shown) and thus, the configuration more easily dissipates heat from the holding member.

Fourth Embodiment

[Configuration]

FIG. 6A shows a light diffusing unit 130 according to the fourth embodiment.

In the second embodiment, the first optical function member directly irradiated by the primary light L1 is the reflection diffusing member 150, the second optical function member is the regular reflection portion 145 formed on the taper surface of the light transmission member 133, and the third optical function member is the light transmission member 133 disposed between the diffusing member 150 and the regular reflection portion 145.

In the third embodiment, the first optical function member directly irradiated by the primary light L1 is the regular reflection portion 250, the second optical function member is the reflection diffusing member 243, and the third optical function member is the light transmission member 133 disposed between the regular reflection portion 250 and the diffusing member 243.

In the present embodiment, however, the first optical function member is the regular reflection portion 250, the second optical function member is the regular reflection portion 145, and the third optical function member is a transmission diffusing member 233 disposed between the regular reflection portion 250 and the regular reflection portion 145 and the present embodiment is different from the first and second embodiments in the above points.

The regular reflection portion 145 in the present embodiment is configured in the same manner as in the second embodiment and the regular reflection portion 250 is configured in the same manner as in the third embodiment.

As shown in FIG. 6B, the diffusing member 233 is formed from a light transmission member 98 and diffusion particles 99 disposed in a dispersed state inside the light transmission member 98. The light transmission member 98 is a silicon resin or the like that allows light to transmit. Any particle that diffuses light like, for example, silica and alumina can be used as the diffusion particles 99. The particle diameter that is substantially equal to the wavelength of the primary light L1 to about 1000 times the wavelength can be used for the diffusion particles.

The diffusion particles 99 may be particles that diffuse-reflect the primary light L1 such as alumina. If such particles are used, diffusion performance is improved. The diffusion particles 99 have transmission with respect to the primary light L1 and may have a different index of refraction from that of the light transmission member 98. The diffusion particles 99 having the above properties are, for example, silica or the like. If such particles are used, the light intensity absorbed by the diffusion particles 99 is reduced and the transmission, that is, the utilization efficiency of the primary light L1 is improved. When the diffusion particles 99 have transmission with respect to the primary light L1, the diffusion particles 99 may be particles in which two kinds of particles or more having different particle diameters and/or indexes of refraction are mixed. In such a case, the diffusion performance of the diffusion particles 99 is adjusted.

The transmission diffusing member 233 is disposed in the entire region where a straight line connecting a point in a valid reflection region of the regular reflection portion 250 and a point in a valid reflection region of the regular reflection portion 145 passes. That is, the transmission diffusing member 233 can realize the gist of the present invention if the primary light L1 is disposed only on an optical path from the first optical function member (regular reflection portion 250) and the second optical function member (regular reflection portion 145). In the present embodiment, the entire region in the truncated conic shape is the diffusing member 233. That is, the diffusing member 233 has a truncated conic shape.

[Operation]

The operation of the primary light L1 emitted from a semiconductor laser light source 111 will be described.

The primary light L1 emitted from the semiconductor laser light source 111 is emitted into the diffusing member 233 by an operation similar to that in the first embodiment.

The primary light L1 irradiates the transmission diffusing member 233 and travels through the diffusing member 233 while bending its optical path due to the diffusion particles 99. That is, the primary light L1 travels while gradually being diffused by the diffusing member 233. For the sake of convenience, the primary light L1 going through the diffusing member 233 will be called diffused light L2 below.

A portion of the diffused light L2 travels toward the regular reflection portion 250 from inside the diffusing member 233 and is regularly reflected by the reflection portion 250 to travel through the diffusing member 233 again. Another portion of the diffused light L2 travels toward the regular reflection portion 145 from inside the diffusing member 233 and is regularly reflected by the reflection portion 145 to travel through the diffusing member 233 again. Still another portion of the diffused light L2 is emitted to the outside from inside the diffusing member 233 via the window portion of an emission portion 242. The diffused light L2 traveling through the diffusing member 233 after regularly being reflected by the regular reflection portion 250 or the regular reflection portion 145 repeats the above operation and a portion thereof is emitted to the outside from the window portion of the emission portion 242.

To sum up, the primary light L1 travels through the transmission diffusing member 233 as the third optical function member and becomes the diffused light L2 by the traveling direction being turned and by being diffused by the third optical function member (diffusing member 233). A portion of the diffused light L2 irradiates the regular reflection portion 250 as the first optical function member and a portion of the diffused light L2 irradiates the regular reflection portion 145 as the second optical function member. The diffused light L2 is caused to turn its traveling direction by the first optical function member (regular reflection portion 250) and the second optical function member (regular reflection portion 145). The diffused light L2 travels through the third optical function member (diffusing member 233) again and a portion of the diffused light L2 is emitted to the outside from the window portion.

[Operation/Effect]

By adopting the above configuration, the primary light L1 is efficiently diffused by the diffusing member 233 and emitted to the outside after sufficiently being diffused by reflection by the two regular reflection portions 145, 250. Thus, when compared with the second and third embodiments, the diffused light L2 that is less likely to cause a speckle or the like is obtained.

In each of the above embodiments, examples in which only one of the first optical function member, the second optical function member, and the third optical function member is a member having the diffusing function, but the present embodiment is not limited to such examples. At least one of the first optical function member, the second optical function member, and the third optical function member may have the diffusing function. Accordingly, the diffusing function can be maximized. Alternatively, even if the level of the diffusing function of each member is degraded, the diffusing function that is sufficient as a whole can be provided. Particularly, if the first optical function member and the second optical function member have the diffusing function and the third optical function member have functions as a light transmission member without having the diffusing function, the diffusion performance is improved and the utilization efficiency of light is enhanced.

Also, in each of the above embodiments, it is desirable to have flat reflection, diffusion, and transmission characteristics with respect to light in the visible light region of 450 nm to 650 nm as optical characteristics with members like the reflecting surface, reflection portion, diffusion particles, and resin used in the first optical function member the second optical function member, and the third optical function member. The value at the bottom of each characteristic is desirably larger than half the peak value. For example, as regards the reflectance with respect to light in the visible light region, the minimum value of reflectance is larger than half the maximum value of reflectance.

In the present invention, an example of combining the semiconductor laser light source 111, the condenser lens 112, and the light guiding member 120 as a light guide path is shown as the primary light source 110, but the present invention is not limited to such an example. The primary light source 110 can be replaced by a solid-state light source such as a light-emitting diode and super luminescent diode (SLD), a solid state laser, a gas laser or the like. The light guiding member 120 can be replaced by a bundle fiber in which a plurality of optical fibers is bundled or a general film or slab waveguide in which a light guide path is formed by providing a distribution of the index of refraction on a resin substrate or semiconductor substrate. Further, the incidence end of the light guide path can be directly joined to the light-emitting surface of the semiconductor laser light source 111, a light-emitting diode, SLD or the like without using the condenser lens 112. In addition, these can appropriately be combined.

The present invention is not limited to the above embodiments unchanged and can be embodied by modifying elements without deviating from the gist thereof in the stage of working. In addition, various inventions can be formed by appropriately combining a plurality of elements disclosed by the above embodiments.

What is claimed is:

1. A light source apparatus having a primary light source that emits primary light and a light diffusing unit that diffuses the primary light,
    wherein the light diffusing unit comprises:
    an incidence portion on which the primary light is incident;
    a diffusing member that diffuses the primary light incident from a side of the incidence portion as diffused light and emits a portion of the diffused light to the side of the incidence portion;
    a reflection portion that regularly reflects or diffuse-reflects the diffused light; and
    an emission portion that emits the diffused light to an outside,
    wherein the emission portion has a window portion so that the portion of the diffused light regularly reflected or diffuse-reflected by the reflection portion is emitted to the outside without reentering the diffusing member from the emission portion.

2. The light source apparatus according to claim 1, wherein the diffusing member and the reflection portion are spaced apart and a light transmission member having a function to transmit the primary light is disposed between the diffusing member and the reflection portion.

3. The light source apparatus according to claim 2, wherein the light transmission member has a truncated conic shape including a first surface of a small diameter, a second surface of a large diameter, and a taper surface and
    the incidence portion is at least a portion of the first surface, the emission portion is at least a portion of the second surface, and the reflection portion is disposed so as to surround the taper surface.

4. The light source apparatus according to claim 3, wherein the light transmission member is formed of glass or resin.

5. The light source apparatus according to claim 2, wherein the diffusing member has the function to transmit and emit a portion of the primary light as transmitted diffused light and the transmitted diffused light is emitted to the outside from the diffusing member only via the emission portion.

6. The light source apparatus according to claim 5, wherein the diffusing member has a cylindrical shape formed from a circular first region facing the incidence portion, a circular third region opposed to the first region, and a second region as a side face sandwiched between the first region and the third region.

7. The light source apparatus according to claim 6, wherein the first region and the second region of the diffusing member are in contact with the light transmission member,
the third region is positioned in the emission portion, and
the emission portion includes the third region and the window portion.

8. The light source apparatus according to claim 6, wherein the first region is in contact with the light transmission member,
the second region and the third region are positioned in the emission portion, and
the emission portion includes the second region, the third region, and the window portion.

9. The light source apparatus according to claim 6, wherein a size of the first region is larger than a beam spot formed in the first region by the primary light.

10. The light source apparatus according to claim 2, wherein the reflection portion is directly formed on a surface of the light transmission member.

11. The light source apparatus according to claim 10, wherein the reflection portion is made of metal.

12. The light source apparatus according to claim 11, wherein the reflection portion has a protective film on an outer surface thereof.

13. The light source apparatus according to claim 1, wherein the primary light source includes a solid-state light source that emits the primary light and a light guide path that guides the primary light.

14. A light source apparatus comprising:
a primary light source that emits primary light;
a first optical function member on which the primary light is incident and which turns a traveling direction of the primary light;
a second optical function member that turns the traveling direction of light derived from the primary light whose traveling direction has been turned by the first optical function member;
a third optical function member disposed on an optical path of the light showing a region between the first optical function member and the second optical function member and traveling from the first optical function member toward the second optical function member; and
a window portion through which, when a portion of the light passes through the first optical function member, the third optical function member, and the second optical function member in this order, the portion of the light is emitted to an outside without reentering the first optical function member, wherein
at least one of the first optical function member, the second optical function member, and the third optical function member has a diffusing function to diffuse the light.

15. The light source apparatus according to claim 14, wherein the first optical function member is a reflection optical function member that reflects the portion of the primary light in an incident side of the primary light,
the second optical function member is a reflection optical function member that reflects the portion of the primary light in the incident side of the primary light, and
the third optical function member is a transmission optical function member that transmits the portion of the primary light.

16. The light source apparatus according to claim 15, wherein regarding a reflectance of the first optical function member and a reflectance of the second optical function member with respect to light in a visible light region, a minimum value of the reflectance is larger than half a maximum value of the reflectance.

17. The light source apparatus according to claim 16, wherein the first optical function member, the second optical function member, and the third optical function member form a diffusing unit that diffuses and emits the light,
the diffusing unit includes an incidence portion on which the primary light is incident and an emission portion from which the light is emitted,
the window portion is a portion of the emission portion;
the first optical function member is disposed near the emission portion;
the second optical function member is disposed in at least a portion of a side face of a three-dimensional object having the incidence portion as a top surface and the emission portion as a bottom surface, and
the third optical function member is disposed in at least a portion of a space inside the three-dimensional object.

18. The light source apparatus according to claim 17, wherein the optical function member having the diffusing function is the first optical function member.

19. The light source apparatus according to claim 18, wherein the first optical function member and the second optical function member are spaced apart and
the third optical function member is disposed between the first optical function member and the second optical function member and has translucency with respect to the primary light.

20. The light source apparatus according to claim 19, wherein the first optical function member is formed from a member having the translucency with respect to the primary light and diffusion particles that are disposed in a dispersed state inside the member and diffuse-reflect the primary light.

21. The light source apparatus according to claim 19, wherein the first optical function member is formed from a translucent member having minute irregularities and having the translucency with respect to the primary light and
an index of refraction of the translucent member to the primary light is different from the index of refraction of the third optical function member.

22. The light source apparatus according to claim 20, wherein the first optical function member has a plane of incidence where the primary light enters the first optical function member and a reflecting surface that reflects the primary light on a plane opposed to the plane of incidence.

23. The light source apparatus according to claim 17, wherein the optical function member having the diffusing function is the second optical function member.

24. The light source apparatus according to claim 23, wherein the second optical function member is optically connected to at least a portion of a surface of the third optical function member.

25. The light source apparatus according to claim 24, wherein the second optical function member is formed by diffusion particles that diffuse-reflect the primary light being applied to at least a portion of the surface of the third optical function member.

26. The light source apparatus according to claim 24, wherein the second optical function member has minute irregularities formed on the surface of the third optical function member.

27. The light source apparatus according to claim 25, wherein the second optical function member has a reflecting surface that reflects the primary light on a plane opposed to the plane optically connected to the third optical function member.

28. The light source apparatus according to claim 17, wherein the optical function member having the diffusing function is the third optical function member.

29. The light source apparatus according to claim 28, wherein the third optical function member is disposed in an entire region where a straight line connecting a point in a valid reflection region of the first optical function member and a point in a valid reflection region of the second optical function member passes.

30. The light source apparatus according to claim 29, wherein the third optical function member is formed from a member having translucency with respect to the primary light and particles that are disposed in a dispersed state inside the member and diffuse-reflect the primary light.

31. The light source apparatus according to claim 29, wherein the third optical function member is formed from a transmission member having transmission with respect to the primary light and particles disposed in a dispersed state inside the transmission member and
   the particles have the transmission with respect to the primary light and have an index of refraction that is different from the index of refraction of the transmission member.

32. The light source apparatus according to claim 30, wherein the particles are particles in which at least two types of particles have different particle diameters and/or indexes of refraction.

33. The light source apparatus according to claim 17, wherein the third optical function member has a truncated conic shape, the incidence portion is the top surface of a small diameter of a truncated cone, the emission portion is the bottom surface of a large diameter of the truncated cone, and the second optical function member is formed on a taper surface of the truncated cone.

34. The light source apparatus according to claim 17, wherein at least two optical function members of the first optical function member, the second optical function member, and the third optical function member have the diffusing function.

35. The light source apparatus according to claim 34, wherein only the first optical function member and the second optical function member have the diffusing function.

* * * * *